United States Patent [19]
Shiraishi et al.

[11] Patent Number: 5,899,943
[45] Date of Patent: May 4, 1999

[54] ARTIFICIAL LIMB INCLUDING KNEE JOINT

[75] Inventors: Norio Shiraishi; Yasukazu Furuichi; Kazuo Nakatani, all of Kobe, Japan

[73] Assignee: Nabco Limited, Hyogo-ken, Japan

[21] Appl. No.: 08/909,960

[22] Filed: Aug. 12, 1997

[51] Int. Cl.[6] .................................................. A61F 2/64
[52] U.S. Cl. ............................................. 623/44; 623/39
[58] Field of Search ................... 623/39–46, 27, 623/57, 38

[56] References Cited

U.S. PATENT DOCUMENTS

| | | | |
|---|---|---|---|
| 1,690,194 | 11/1928 | Girton | 623/39 |
| 1,966,574 | 7/1934 | Wenneborg | 623/32 |
| 2,450,728 | 10/1948 | Havens | 623/52 X |
| 2,533,008 | 12/1950 | Hanson | 623/26 |
| 2,794,987 | 6/1957 | Oliver | 623/43 |
| 4,152,787 | 5/1979 | Meggyesy | 623/44 |
| 4,320,747 | 3/1982 | Daniell | 623/39 X |
| 5,044,360 | 9/1991 | Janke | 623/39 X |

FOREIGN PATENT DOCUMENTS

| | | | |
|---|---|---|---|
| 1225626 | 2/1961 | France | 623/44 |
| 84 11 93 | 6/1952 | Germany | 623/27 |
| 8-229059 | 9/1996 | Japan | 623/39 |

Primary Examiner—David H. Willse
Attorney, Agent, or Firm—Kane, Dalsimer, Sullivan, Kurucz, Levy, Eisele and Richard, LLP

[57] ABSTRACT

Paying attention to the mechanical play between the first and second support members for supporting opposite end portions of a knee axis and a brake block located between the support members, the present invention chiefly aims at removing the play in the direction of an axis of the knee axis in an effective and a reliable manner. In order to achieve this object, according to the present invention, a plurality of spacer members are inserted between each support member and the brake block such that the spacer members may slide on the mutual abutment surface. Each spacer member is of a ring type. The spacer members are fitted to and supported by the knee axis in a state that the spacer members are overlaid one upon another in the axial direction of the knee axis. In order to enhance the smooth sliding on the abutment surface, the spacer members are preferably made of resin material. In order to enhance the smoother sliding, at least one spacer member having the abutment surface is more preferably made of resin of low friction, such as oil-contained resin or phenol resin. The remaining spacer member contacting the resin of low friction may be made of such resin as polyacetal, polyamide and tetraethylene fluoride. Most preferably, one spacer member is made of oil-contained polyacetal resin which is especially excellent in low friction, and the remaining spacer contacting the first-mentioned spacer member is made of non-oil contained polyacetal resin.

13 Claims, 9 Drawing Sheets

FIG. 10

ARTIFICIAL LIMB INCLUDING KNEE JOINT

BACKGROUND OF THE INVENTION

This invention relates to a prosthetic limb including a knee joint, and more particularly to an artificial limb including a single axis knee (knee joint member). More particularly, it is directed to an artificial limb which is so quiet in operating noise that the user sometimes forgets his/her wearing of the artificial limb, and which can provide the perception of comfortableness to the user.

In general, artificial limbs including a knee axis comprises an upper member including a knee plate to which load of the user (amputee) applies, a lower member including a hollow frame extending from the knee portion to the foot portion and connected to the upper member at the knee portion, and a knee axis rotatably supporting the upper and lower members, opposite end portions of the knee axis being supported respectively by a first and a second support member which are provided on the hollow frame. One typical example of this type of prosthetic leg is an above-knee prosthesis which includes a socket supported on an upper end of the knee plate of the upper member and adapted to receive the stump, and a foot member supported on a lower end of the lower member.

There are two types of knee axes for interconnecting the upper and lower members. The first is of a single axis knee (joint) (hereinafter the knee as a joint is simply referred to as "knee" or "knee joint"), and the second is of a polycentric-axes knee (joint) including a plurality of links and variable in the center of rotation in accordance with a bending angle of the knee. The single axis knee joint is simple in construction compared with the polycentric-axes knee joint and can fully endure the dynamic motion of the user as in sports. For this reason, the single axis knee joint is suited to those who need a huge amount of activity.

Because of the construction that the upper and lower members are freely rotatable about the knee axis, it is required for such an artificial limb as including a single axis knee to be designed to generate a proper braking force. As means for generating this braking force, three types were heretofore known. The first type is disclosed by U.S. Pat. No. 3,863,274 (corresponding to Japanese Patent Publication No. 52(1977)-46432 or Japanese Patent Publication No. 57(1982)-41943), in which a braking force is generated by reducing the diameter of a through-hole formed in a brake block. The second type is disclosed by U.S. Pat. No. 4,152,787, in which a braking force is generated by pressing movable discs against stationary discs utilizing the motion of a wedge. The third type is disclosed by U.S. Pat. No. 4,206,519, in which a brake shoe is located inside a hollow brake drum and a braking force is obtained by enlarging the diameter of the brake shoe. Those means of the above-mentioned first to third types are common to each other in the respect that the brake means is a load brake means of a load responsive type in which the braking force generating means are arranged around the knee axis and a braking force thereof is generated by load of the user applied thereto. From a view point of a smaller space required, the first type is the best.

Incidentally, it is required for the single axis knee that the connection around the knee axis or shaft is tightened because load of the user is concentrated on the single knee axis. From this view point, British Laid-Open Patent Publication No. 2,296,442 (corresponding to Japanese Laid-Open Patent Publication No. 8(1996)-229055) discloses an idea that a hollow frame made of a fiber-reinforced plastic is provided on opposite ends thereof with non-circular first and second attaching holes and first and second support members made of metal are cold fitted to the attaching holes, respectively. This British Publication also teaches that a axis is fitted from outside the frame through the first and second support members, and the axis, i.e., knee axis, is fixed by inserting split-pins into opposite end portions of the axis, respectively.

According to the technology disclosed by this British Laid-Open Patent Publication No. 2,296,442 (corresponding to Japanese Laid-Open Patent Publication No. 8(1996)-229055), the first and second support members can be firmly secured to the frame. This arrangement provides the advantage in that a rotation stopper for stopping the rotation when the artificial limb is in a stance phase or swing phase, can be formed integrally with each support member. However, there still remains room for improvement from the view points that play in the axial direction between the brake block around the knee axis and the first and second support members is removed, that play in the rotational direction between the first and second support members and the knee axis, and that play between the member for fixing the knee axis and the frame. The above play appeared to the various places causes a physical contact between adjacent members, thereby generating noises and rubbing which often provide the perception of uncomfortableness to the user.

As one attempt for removing play in the axial direction of the knee axis, there can be contemplated a method for providing a spacer between the support members on the frame side and the brake block. However, it became known that this spacer is subjected to wear caused by the relative rubbing motion generated between the support members or the brake block and the surface of the spacer facing those support members or brake block. The reason is that the spacer rotates together with the knee axis. The wear of the spacer results in generation of play (chattering) in the axial direction. In addition, there is a possibility that the frictional powders produced by wear invade into the interior of the brake block to degrade the braking performance. The problems mentioned above are not only inherent in the first type load brake means but also in the second or third type means.

SUMMARY OF THE INVENTION

The present invention has paid attention to the fact that by lessening the operating noise of the artificial limb, the perception of comfortableness can be given to the user. It is, therefore, a first object of the present invention to effectively and assuredly remove the play in the axial direction of the knee axis by providing a unique spacer means between the first and second support members for supporting the opposite end portions of the knee axis and the load brake means located between the support members.

In order to achieve this first object, the spacer means employed in the present invention includes at least two spacer members, and the spacer means are rotatable relative to each other while sliding on the mutual abutment surface. Each spacer member is of a ring type. The spacer members are fitted to and supported on the knee axis in their axially overlaid fashion. In order to enhance the smooth sliding on the abutment surface, the spacer members are each preferably made of resin material. In order to enhance a smoother sliding, at least one spacer member having the abutment surface is particularly preferred to be made of resin of low friction such as oil-contained resin or phenol resin. On the other hand, the remaining spacer member to be contacted with the resin of low friction is preferably selected from those having light weight, low friction and low cost. For example, the material for the remaining spacer member may include such resin as polyacetal, polyamide, and tetraethylene fluoride. Most preferably, one spacer member is made of oil-contained polyacetal resin which is particularly excellent in low friction, and the remaining spacer member to be contacted therewith is made of non-oil-contained polyacetal resin. The spacer means may consist of two or three spacer members. A thinner shim than the spacer members may be applied thereto in order to adjust the thickness in accordance with necessity. In case the shim is employed, it is accepted that the shim itself is served as one of the spacer members constituting the spacer means and its abutment surface with respect to the remaining spacer member causes the sliding. It is also an interesting alternative that the shim itself is used only for the purpose of adjustment of the thickness and integrally formed with the adjacent remaining spacer member, etc. It is also accepted that an opposite surface to the abutment surface causing the sliding is provided with a resilient member such as an O-ring, so that play or chattering between the spacer means and the load brake means, and between the spacer means and the frame side is absorbed by the resilient deforming force of the resilient member.

It is another object of the present invention to remove play in the rotational direction between each support member and the knee axis by firmly securing the first and second support members on the frame side to the opposite end portions of the knee axis. That is, it is a second object of the present invention to integrally form the knee axis with the frame side through the first and second support members secured to the frame side.

In order to achieve this second object, according to the present invention, a selected one of the knee axis and the first and second support members is provided with a non-circular recess and the other non-selected one is provided with a protrusion corresponding to the recess, so that the knee axis is secured to the bearing member by press fitting the protrusion into the recess. The press-fit means is preferably a method utilizing the cool fitting. In order to enhance an easy connection between each end portion of the knee axis and each support member, the non-circular recess portion is most preferably a groove having a pair of inner walls extending in parallel relation along the opposite sides thereof, with at least one end of the groove in the radial direction thereof being opened. With the recess thus designed, the protrusion and the recess can easily be connected by inserting the protrusion into the recess through one open end of the groove. The material of the support members and the knee axis should be selected from those which have a certain degree of difference in thermal expansion coefficient. For example, the support members may be made of aluminum or aluminum alloy, and the knee axis may be made of stainless steel.

It is a third object of the present invention to hold the frame from inside and outside in a sandwiching fashion at each support member located at each end portion of the knee axis, so that play of the frame is prevented from occurring.

In order to achieve the third object, according to the present invention, in addition to the arrangement that the first and second support members are press fitted respectively to the first and second non-circular attaching holes formed in the frame, the following constitutional features A through C are employed with a view to supporting the knee axis.

A. The first and second support members being provided, in addition to the protrusions, with flange portions each having a larger diameter than the protrusions, an end face of each of the protrusions being projected outwardly of an outer surface of the hollow frame when secured to the hollow frame, the flange portion pressing a peripheral edge portion of each of the attaching holes in an inner surface of the hollow frame;

B. the first and second support members being provided on one surfaces thereof respectively with grooves which are radially opened, each end portion of the knee axis being attachable to a central portion of each of the support members through the grooves; and C. bolt members coaxial with the knee axis being threadingly joined to end portions of the knee axis, respectively, the bolt members being each provided with a head portion of an enlarged diameter reaching the peripheral edge portion of each of the attaching holes, the hollow frame being supported in a sandwiched fashion between the flange portions of the support members and the head portions of the bolt members.

In order to achieve the third object more effectively, in a preferred embodiment of the present invention, one surface of the head portion of each of the bolt members opposite the support members is provided with a recess capable of receiving therein the protrusions of the support members which are projected outwardly of the outer surface of the hollow frame, and a ring-shaped protrusion surrounding the recess, the non-circular protrusion of each of the support members being provided with a releasing groove for releasing the protrusion of the head portion of each of the bolt members. The hollow frame is preferably made of light and rigid fiber-reinforced plastic, while the first and second support members including the flange portions and the first and second bolt members including the head portions are made of metal material. Although the fiber-reinforced plastic itself cannot be said as having a sufficient resistance against tearing compared with the metal material, it has a sufficient resistance against the surface pressure.

Furthermore, the present invention can be widely applied to artificial limbs including a single axis knee joint. In particular, by applying the present invention to an artificial limb which includes a cylinder assembly for assisting the walking of the user between the upper member and the lower member, not only a quiet operating noise can be realized but also a walking style resembling a natural walking style can be realized, which provides a more pleasant perception of comfortableness to the user. The cylinder assembly for assisting the walking is located on a rear part of the knee portion. The cylinder assembly is in a reducing stroke where a length of the cylinder is reduced when the knee is bent, and the cylinder assembly is in an extending stroke where the length of the cylinder is enlarged when the knee is extended.

BRIEF DESCRIPTION OF THE DRAWINGS

FIG. 3 is an illustration, showing a state of a brake block when a brake is in a non-operating condition, (a) is a sectional view, showing an internal construction of the brake block, and (b) is a view, showing a positional relationship between the brake block and a knee plate;

FIG. 7 is a partial view, showing a supporting form of each axis support member for a frame, (a) is a sectional view taken along a longitudinal direction of the frame, and (b) is a view of the axis support portion when viewed from the inside of the frame;

FIG. 8 is an illustration of the axis support member, (a) is a view when viewed from one side of the axial direction, (b) is a side view and (c) is a view when viewed from the other side of the axial direction;

FIG. 9 is an illustration, showing a knee axis, (a) is a sectional view taken along the axial direction, and (b) is a side view.

DESCRIPTION OF THE PREFERRED EMBODIMENT

Figure 1:
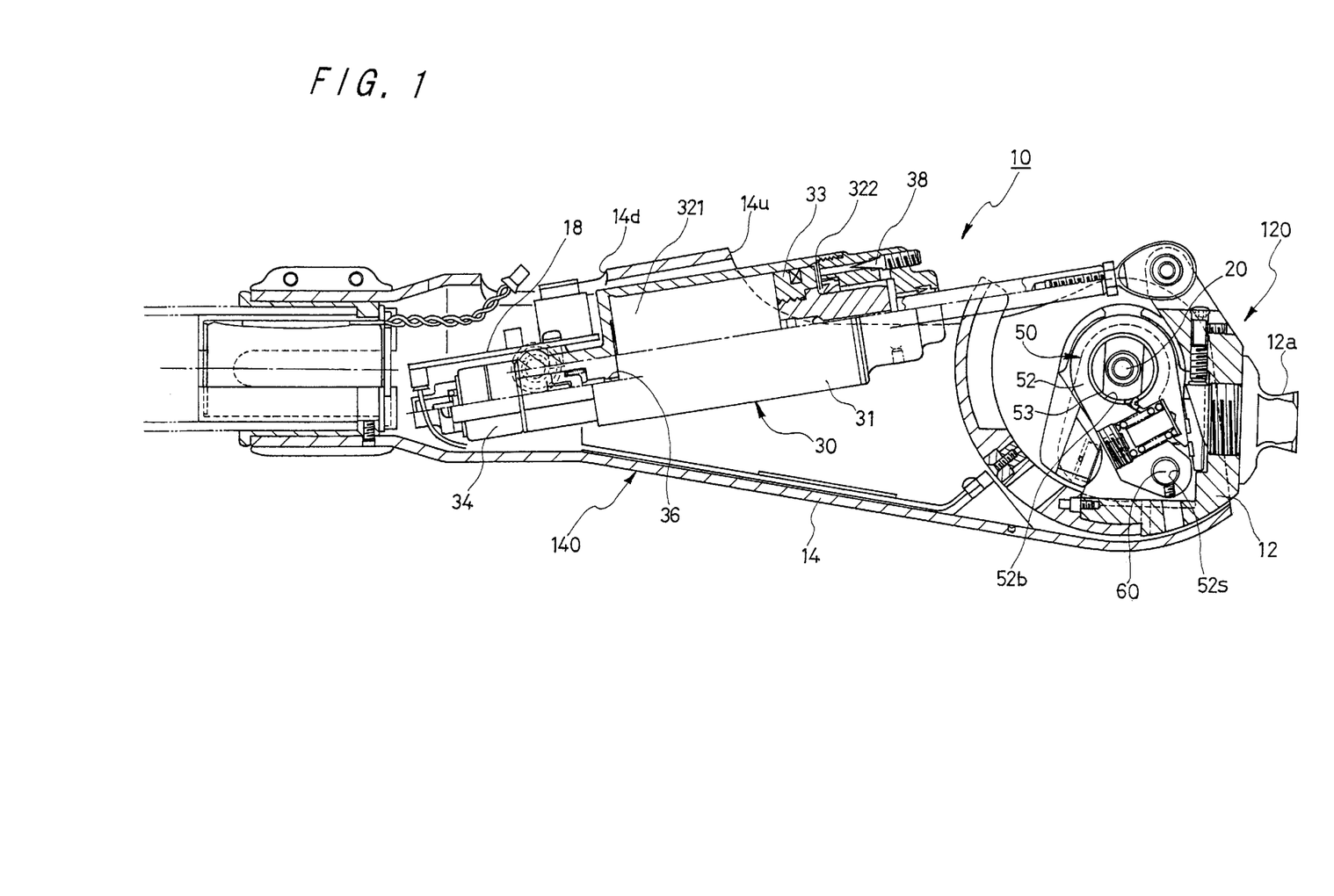
FIG. 1 is a sectional view, showing an overall construction of an above knee prosthesis incorporated with the present invention when the knee is extended.
Figure 2:
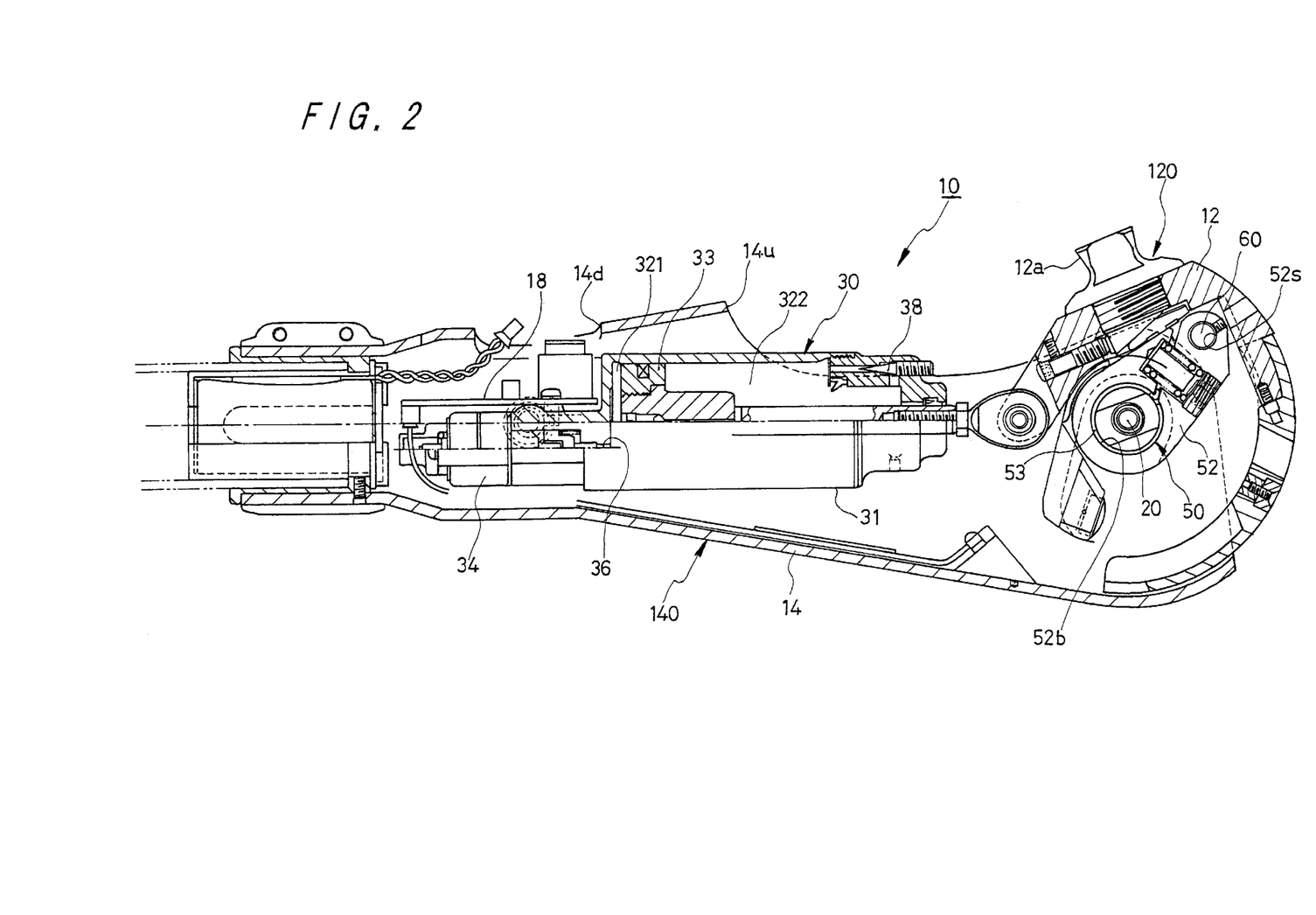
FIG. 2 is likewise a sectional view but the knee of FIG. 1 is bent.

First, an overall construction of an above knee prosthesis 10 incorporated with the present invention is described with reference to FIGS. 1 and 2.

The above knee prosthesis 10 is an artificial leg for those who lost the knee. The above knee prosthesis 10 comprises an upper member 120 including a knee plate 12 having a knee-like configuration, a lower member 140 chiefly consisting of a hollow frame 14 extending from the knee portion towards the foot portion, and a knee axis 20 for rotatably interconnecting the lower member 140 and the upper member 120 at the knee portion. The knee plate 12 is made of an aluminum alloy. The knee plate 12 integrally supports on a part thereof a connector 12a for connecting a socket, not shown. On the other hand, the hollow frame 14 as a chief component element of the lower member 140 is made of a fiber-reinforced plastic having a thickness of approximately 3 mm. The hollow frame 14 is provided at its rear part with an upper opening 14u and a lower opening 14d. The upper opening 14u is an opening through which various parts are inserted and built in the interior of the hollow frame 14. It is also an opening for preventing the interference between an air cylinder assembly 30 and the hollow frame 14. The lower opening 14d is an opening through which an electrical connection to an electrical substrate 18, which is disposed within the hollow frame 14, is achieved. The air cylinder assembly 30 may be of the type which is disclosed in U.S. Pat. No. 5,405,407, or in Japanese Laid-Open Patent Publication No. 9(1997)-551. The assembly 30 comprises a cylinder body 31, a piston 33 for defining a first chamber 321 and a second chamber 322 within the cylinder body 31, a variable throttle valve 36 controlled by a stepping motor 34 so as to be opened by an appropriate degree in accordance with the walking speed of the user, a stationary diaphragm (or stop) 38 which can be manually adjusted, and some others. Owing to this arrangement, the air cylinder assembly 30 is capable of controlling the bending and extending action of the knee so that the action may resemble the natural walking style in a swing phase in which the above knee prosthesis 10 is moved away from the surface of the floor or the like.

The above knee prosthesis 10 includes a load brake means 50 around the knee axis 20. This load brake means 50 is of the afore-mentioned first type, in which a braking force is generated by reducing the diameter of a through-hole 52b of a brake block 52 which embraces the knee axis 20. The brake block 52 is made of titanium alloy. In addition to the large through-hole 52b for receiving therein the knee axis 20, the brake block 52 is further provided with a small through-hole 52s. This small through-hole 52s is located in the vicinity of that end of the brake block 52 which is located opposite to the end where the large through-hole 52b is formed. The brake block 52 with the knee axis 20 put into the large through-hole 52b through a metal bush 53 and with a connecting pin 60 received in a small through-hole 52s is set inside the knee plate 12. Opposite end portions of the knee axis 20 are supported respectively by a first support member 71 and a second support member 72 on opposite sides of the hollow frame 14. Opposite end portions of the connecting pin 60 are supported within a support hole 12h formed in the bush 12b (see FIG. 4(b) of knee plate 12. The connecting pin 60 can also be inserted into the through-hole 52s through a bush. In this case, the material of the bush inserted into the through-hole 52s is preferably more readily deformable than that of the knee plate 12. For example, while the knee plate 12 is made of aluminum material, the bush may preferably be made of bronze which is readily deformable compared with aluminum. By appropriately selecting the material in this way, the force applied to the brake block 52 from the knee plate 12 through the connecting pin 60 can be dispersed in the radial direction of the connecting pin 60 through the bush. For this reason, in spite of the fact that a comparatively light material is used as the material for the knee plate 12, the possible damage to the knee plate 12 can effectively be prevented from occurring. The connecting pin 60 itself can be secured to the knee plate 12 through a machine screw 62 disposed at one side thereof.

The brake block 52 is further provided with a split groove 54 extending for communication from its outer surface to the large through-hole 52b and a blind hole 56 intersecting the split groove 54. The split groove 54 is a groove for dividing the brake block 52 into two parts so that the diameter of the large through-hole 52b is reduced. On the other hand, the blind hole 56 is a hole for receiving therein a coiled spring 57. An adjusting plug 58 is threadingly connected to an opening portion of the blind hole 56. By appropriately adjusting the degree of connection of the adjusting plug 58, the compressed condition of the inside coiled spring 57 can be adjusted and the working degree of the brake of the load brake means 50 can be adjusted. A first and a second brake pad 41, 42 each having a wedge-like configuration are arranged between the knee plate 12 and the brake block 52. A rubber member 41r is fixedly seized to the first brake pad 41 facing the brake block 52. A distal end of an adjusting screw 44 is in contact with one surface of the second brake pad 42. Owing to this arrangement, by turning this adjusting screw 44, the first brake pad 41 can be displaced through the second brake pad 42. Through the adjustment of the adjusting screw 44, a gap between the brake block 52 and a plane including the rubber member 41r of the first brake pad 41 can be varied in size. The adjusting screw 44 can also be retained its position after adjustment by the machine screw 45.

Figure 3A:
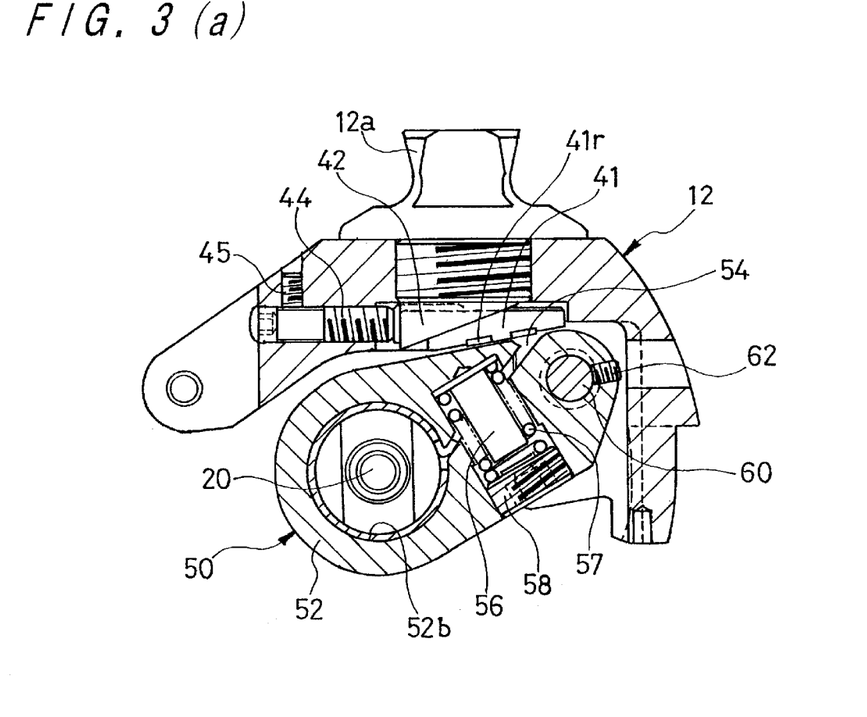
Figure 3B:
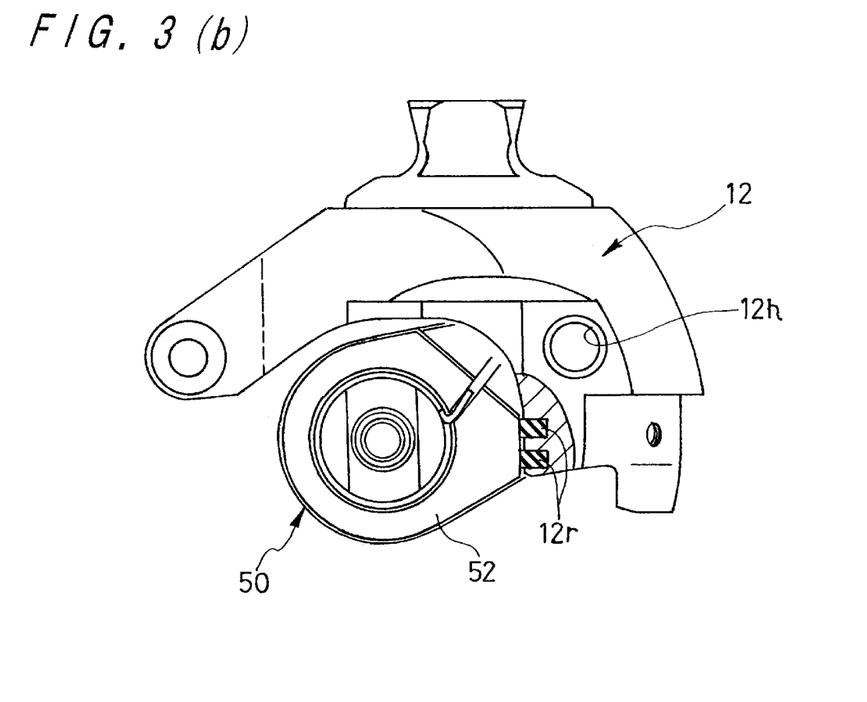
Figure 4:
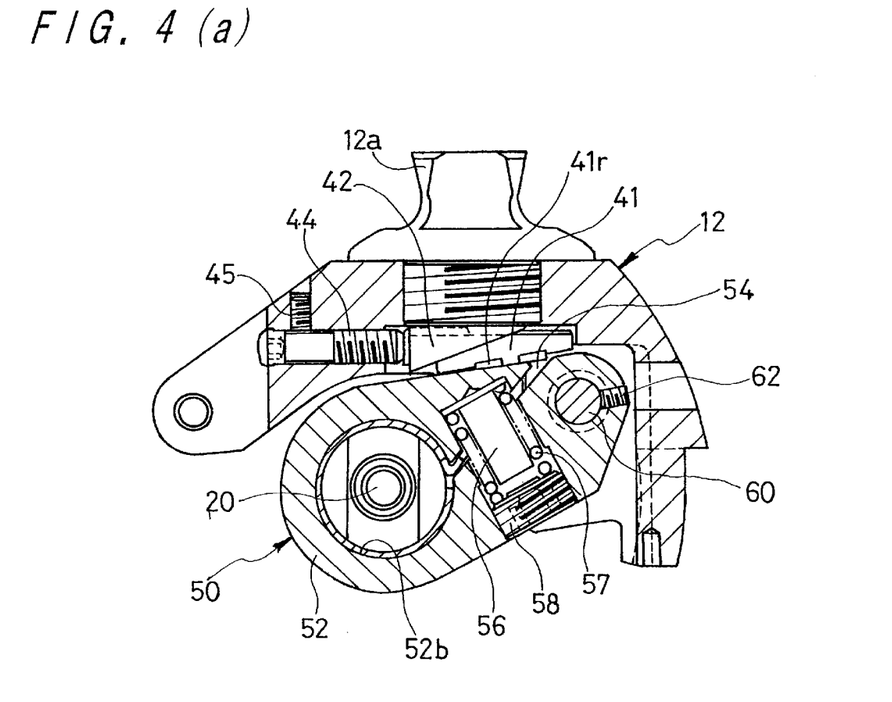
FIG. 4 is an illustration showing a state of the brake block corresponding to FIG. 3 when the brake block is in an operating condition, (a) is a sectional view, showing an internal construction of the brake block, and (b) is a view, showing a positional relationship between the brake block and the knee plate.

When the brake is in its operating condition upon application of the load of the user through the knee plate 12, the rubber member 41r of the first brake pad 41 is in contact with the brake block 52 side (see FIG. 4a). In contrast, when the brake is in its non-operating condition, the rubber member 41r of the first brake pad 41 produces a small gap between the first brake pad 41 and the brake block 52 (see FIG. 3a). On the other hand, the remaining part of the brake block 52 contacts the knee plate 12 side when the brake is in its non-operating condition, and a small gap is formed between the knee plate 12 side and the brake block 52 when the brake is in its operating condition. Accordingly, the brake block 52 hits the other member, namely, the first brake pad 41, or the knee plate 12 depending on whether or not the brake is operating. The rubber member 41r of the first brake pad 41 side is functioned as a damping member for damping the noises caused by hitting. At the same time, another damping member 12r made of resilient material such as rubber is also provided on the knee plate 12 side.

Figure 5:
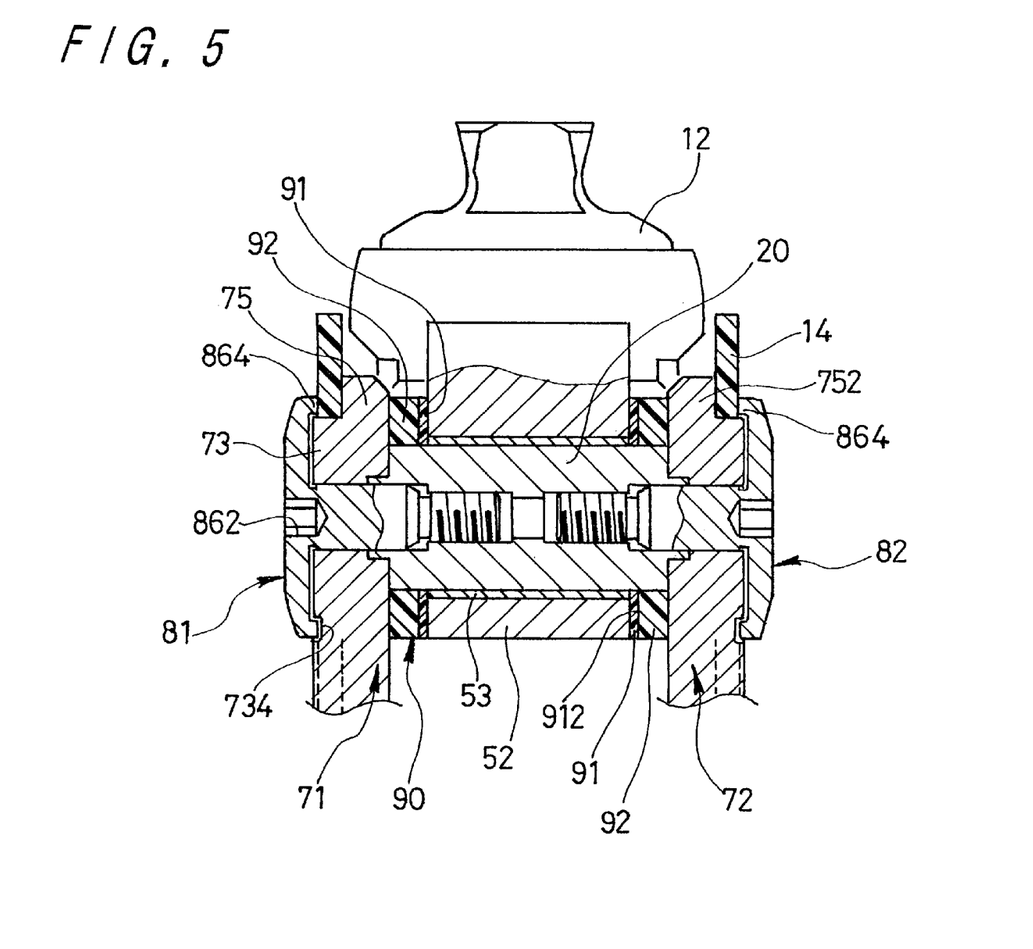
FIG. 5 is a sectional view taken along an axial direction of a knee axis portion, showing a first example of spacer means according to the present invention.

As apparent from the sectional view taken in the direction of the axis of the knee axis 20 of FIG. 5, the first and second support members 71, 72 are supported by the frame 14 made of fiber-reinforced plastic. The knee axis 20 is supported between the first support member 71 and the second support member 72. Here, the first and second bolt members 81, 82 contribute not only in supporting the first and second support members 71, 72 by the frame 14 but also in supporting the knee axis 20 by the support members 71, 72, so that a more reliable supporting structure is ensured. Through this supporting structure, the knee axis 20 is integrally united with the first and second support members 71, 72 and the frame 14. This supporting structure of the knee axis 20 will be described in detail later. Looking into such knee axis 20 portion, it will be known that the first and second support members 71, 72 are located at the opposite end portions of the knee axis 20, and the brake block 52 including the metal bush 53 is located between the first support member 71 and the second support member 72. The brake block 52 connected to the knee plate 12 and the first and second support members 71, 72 connected to the frame 14 can relatively rotate about the knee axis 20. Here in this embodiment, the spacer means 90 is arranged on the axis of the knee axis 20 and between the brake block 52 and the first and second support members 71, 72. The spacer means 90 consists of two spacer members 91, 92 each having a ring-like configuration. The spacer member 91 is made of oil-contained polyacetal resin and thin (approximately 1 mm), while the other spacer member 92 is made of non-oil-contained polyacetal resin and comparatively thick (approximately 2 mm to 3 mm). The two spacer members 91, 92 are overlaid one upon the other and supported by the knee axis 20 in that condition. The spacer means 90, firstly, fills a gap between the brake block 52 and the first and second support members 71, 72 and removes the play or chattering in the axial direction between those members which rotate relative to each other. The spacer means 90, secondly, serves the inside thereof, namely, an abutment surface 912, which the two spacer members 91, 92 contacting each other contact, as a sliding surface, so that a smooth rotational motion can be obtained between the lower member 140 side including the first and second support members 71, 72 and the upper member 120 side including the brake block 52. The material of the non-oil-contained spacer member 92 may include, In addition to the polyacetal resin, other resin such as polyamide and tetraethylene fluoride.

Figure 6:
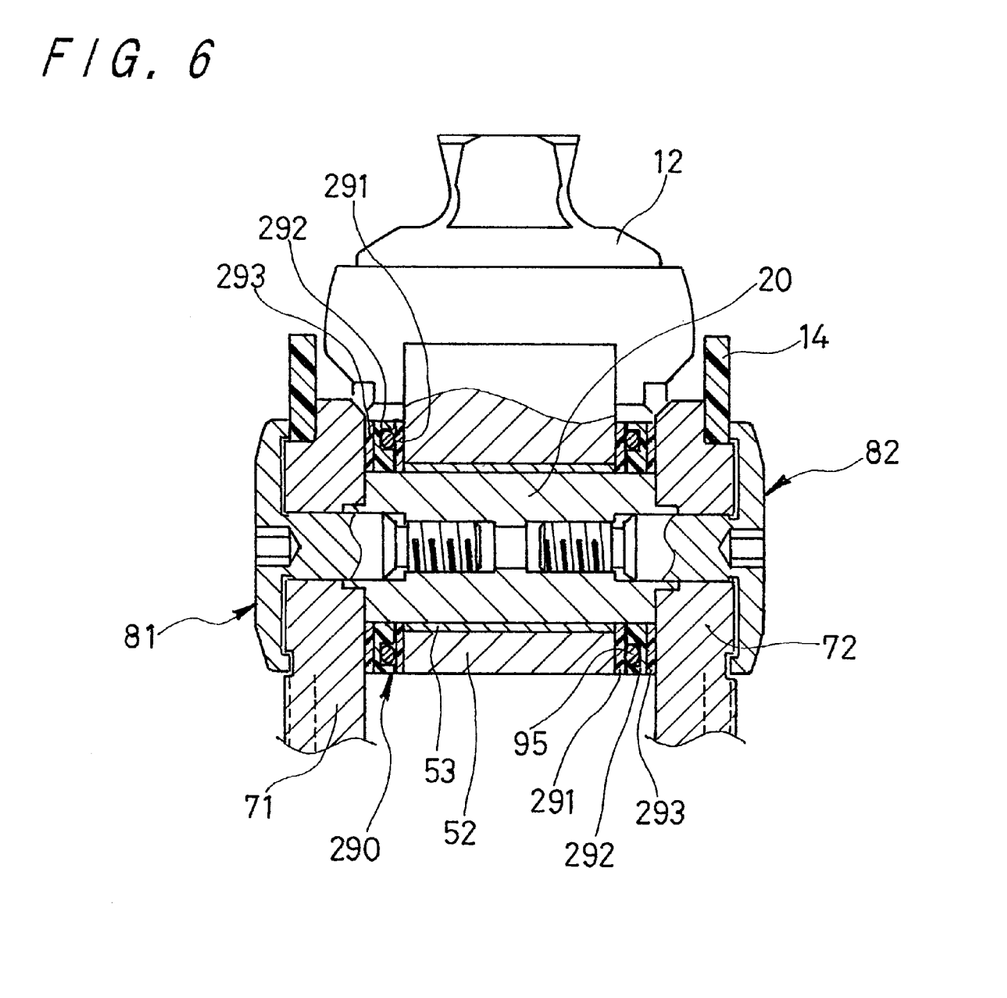
FIG. 6 is a sectional view, like FIG. 5, showing a second example of spacer means according to the present invention.
Figure 7A:
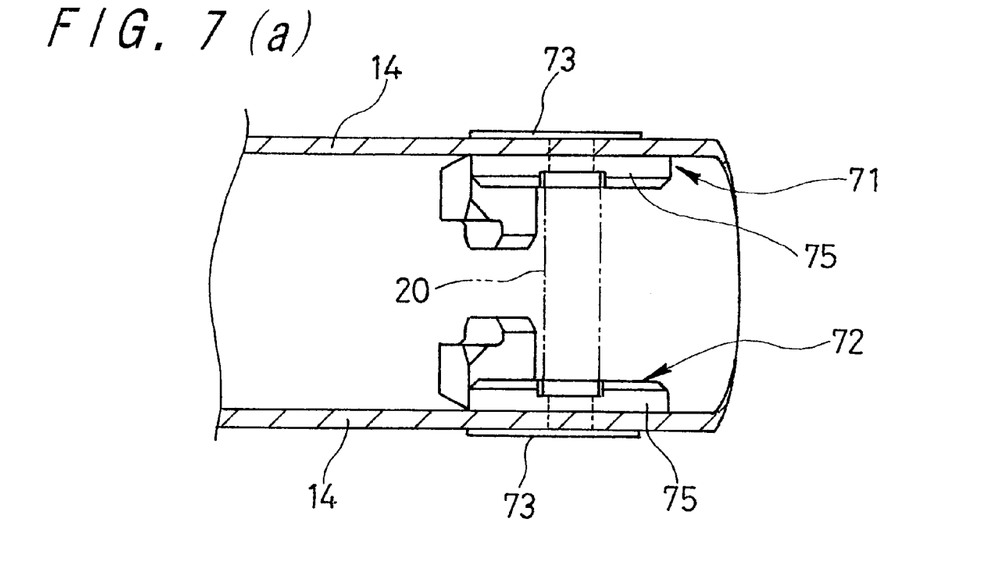
Figure 7B:
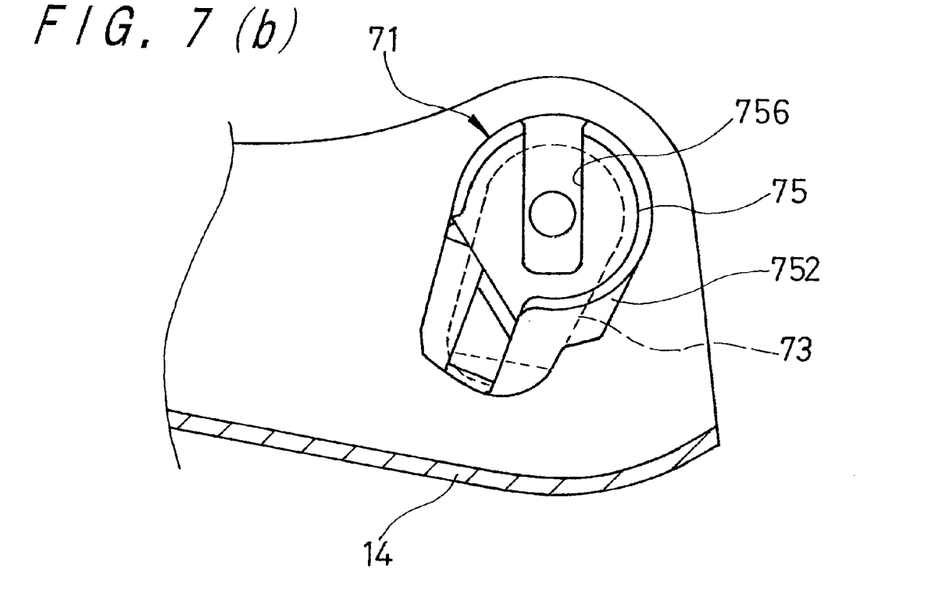

FIG. 6 shows another spacer means 290. In this second example, the spacer means 290 arranged between the brake block 52 and the first and second support members 71, 72 consists of three spacer members 291, 292 and 293. The three spacer members 291, 292 and 293 are laid one upon another. The central spacer member 292 is made of thick non-oil-contained resin as in the spacer member 92, but the member 292 is provided at one surface thereof with a groove within which an O-ring 95 is supported. The spacer member on one side of this central spacer member 292 is a spacer member 291 made of oil-contained resin as in the spacer member 91. The remaining spacer member on the side where the O-ring 95 is located is a spacer member 293 made of non-oil-contained resin such as polyamide resin. In this spacer means 290, the abutment surface between the spacer member 291 made of oil-contained resin and the spacer member 292 made of non-oil-contained resin is also served as an internal sliding surface. The spacer means 290 includes therein the O-ring 95 and can effectively absorb the play or chattering between the brake block 52 and the first and second support members 71, 72 by resilient deformation of the O-ring 95 and without using a shim.

Next, with reference to FIGS. 7 through 10, as well as FIGS. 5 and 6, a method for securing the first and second support members 71, 72 to the frame 14 and a method for securing the knee axis 20 to the first and second support members 71, 72 will be described. Each of the first and second support members 71, 72 is of a laterally symmetrical configuration. Therefore, the method for securing one of the support members 71, 72 to the frame 14 is the same as the method for securing the other support member 71, or 72 to the frame 14. The same is true to the method for securing the knee axis 20 to the first and second support members 71, 72.

Figure 8:
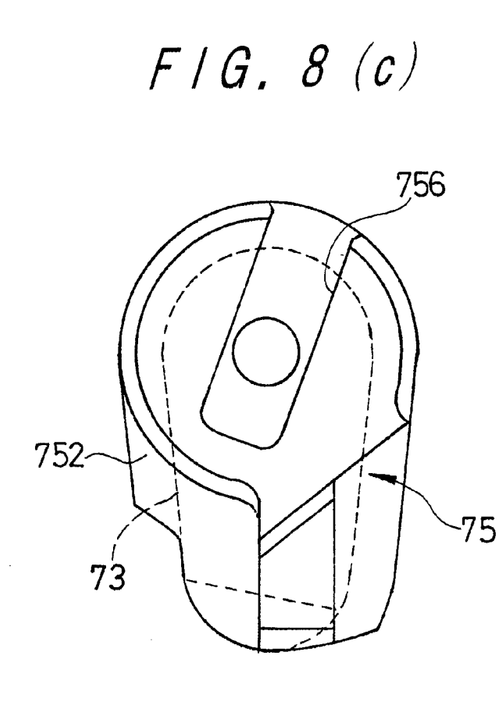

FIG. 8 shows the first and second support members 71, 72. The support members 71, 72 are each made of aluminum material. Particularly, as shown in FIG. 8, each of the support members 71, 72 includes a protrusion 73 nicely fitted to a non-circular attaching hole formed in the frame 14, and an enlarged diameter portion 75 located on the back of the non-circular protrusion 73. The surfaces of the support members 71, 72 are preferably subjected to alumite treatment so that the corrosion resistance of the surface is increased. The enlarged diameter portion 75 is provided with a flange portion 752 which spreads radially outwardly of the protrusion 73, a stopper portion 754 for supporting a stretched stopper rubber as a stopper when the artificial limb is extended, and a groove 756 opening in the radial direction and capable of attaching the end portions of the knee axis 20 to the central portions of the first and second support members 71, 72. On the other hand, the non-circular protrusion 73 is slightly thicker than the frame 14 (for example, the thickness of the frame 14 is 3.0 mm while the thickness of the protrusion 73 is 3.5 mm). Moreover, the outside diameter of the protrusion 73 is larger by a tightening width (for example, 0.2 mm to 0.3 mm) than the attaching hole of the frame 14 side. For securing this protrusion 73 to the frame 14 side, the same cool fit as discussed in the aforementioned British Laid-Open Patent Publication No. 2, 296,442 is utilized. When the protrusion 73 is press fitted into the attaching hole of the frame side 14, an end face of the protrusion 73 projects slightly outwardly of the outer surface of the frame 14 due to its thickness. The enlarged diameter portion 752 contacts the peripheral edge portion in the inner surface of the frame 14 so that the peripheral edge portion of the attaching hole can be supported.

Figure 9:
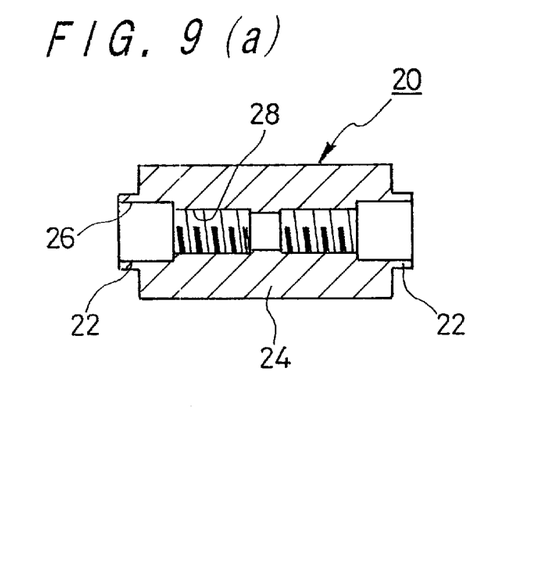
Figure 10:
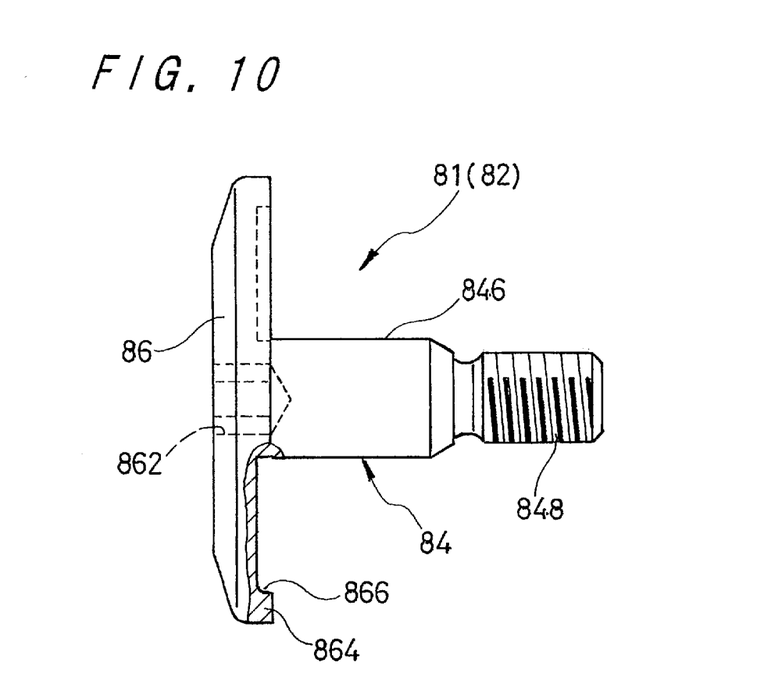
FIG. 10 is a side view, partly cut-away, of a bolt member.

FIG. 9 is a view, showing the knee axis 20 supported by the first and second support members 71, 72. The knee axis 20 is made of stainless steel. The knee axis 20 includes a sectionally circular axis body 24 having an outside diameter matching with the inside diameter of the metal bush 53 on the brake block 52 side, a two-surfaces width portion 22 (this portion 22 includes two side surfaces 22a, 22b parallel to each other, and the width of the side surfaces 22a, 22b is matched with the size of the groove 756 of each support member 71, 72) located on each end portion of the axis body 24, a central hole 26 opening to the end face of the portion 22, and an internally-threaded hole 28 coaxial with the central hole 26. The central hole 26 and the internally-threaded hole 28 are arranged at each end portion of the axis body 24 of the knee axis 20, so that the axis portion 84 of the bolt member (that is, the first and second bolt members 81, 82 having the same configuration and construction) of FIG. 10 is either fitted or threadingly engaged therewith. The axis portion 84 of the bolt members 81, 82 includes a portion 846 fitted to the central hole 26, and an externally-threaded portion 848 threadingly engaged with the internally-threaded hole 28. The bolt members 81, 82 are each provided on end portions of the axis portion 84 with a head portion 86 of an enlarged diameter. This head portion 86 has a size reaching the peripheral edge portion of the attaching hole of the frame 14. The head portion 86 is provided at its central portion with a hexagon socket 862 for inserting a tool for tightening the bolt members 81, 82. The head portion 86 is also provided at its peripheral edge portion facing the frame 14 with a protrusion 864. This protrusion 864 is of a ring-like configuration extending over the full circumference. Owing to this feature, the protrusion 864 is formed with a recess 866 on its inner peripheral side.

Please watch carefully FIGS. 10 and 8 while comparing the protrusions 864 and recess 866 of the bolt members 81, 82 of FIG. 10 with the protrusions 73 of the support members 71, 72. When securing the bolt members 81, 82 to the support members 71, 72 which are secured to the frame member 14 and the knee axis 20 which is assembled to the support members 71, 72, the bolt members 81, 82 are gradually progressed in the axial direction and the protrusion 864 of the head portion 86 comes to hit the outer surface of the frame 14. Since the protrusions 73 of the support members 71, 72 projecting outwardly of the frame 14 are each provided with a release groove 734 for releasing the protrusion 864 of the head portion 86, the protrusion 864 on the bolt members 81, 82 side is rotated through the release groove 734 and receives a part of the protrusion 73 in the recess 866. At the same time, the protrusion 864 presses one surface of the protrusion 864 against the outer surface of the frame 14 by a threadingly connecting force. By doing so, the protrusion 864 on the bolt members 81, 82 side supports the frame 14 in a sandwiched fashion between the protrusion 864 and the flange portion 752 of the support members 71, 72 within the frame 14.

What is claimed is:

1. An artificial limb including a knee joint, comprising an upper member including a knee plate to which load of a user of said artificial limb is applied; a lower member including a hollow frame extending from a knee portion towards a foot portion and connected to said upper member at the knee portion; a knee axis for rotatably interconnecting said upper and lower members, opposite end portions of said knee axis being supported respectively by a first and a second support member which are provided on said hollow frame; and load brake means connected to the knee plate located on an outer periphery of said knee axis and between said first support member and said second support member and for generating a braking force in accordance with load applied through said knee plate; said knee axis supporting spacer means each between said first and second support members and said load brake means, said spacer means including at least two spacer members each made of resin material, said at least two spacer members being rotatable relative to each other while sliding on abutment surfaces thereof.

2. An artificial limb according to claim 1, wherein said knee axis is secured to said hollow frame through said first and second support members.

3. An artificial limb according to claim 1, wherein said load brake means includes a brake block pinned to said knee plate, said brake block having a through-hole for inserting therein said knee axis, said through-hole being reduced in diameter to tighten said knee axis when load of the user is applied thereto through said knee plate.

4. An artificial limb according to claim 3, wherein said knee plate and said brake block each have a portion to which said artificial limb contacts in accordance with extending and bending of said artificial limb and said portion is provided with a damping member.

5. An artificial limb according to claim 3, wherein a bush, which is more readily deformed than the material of said knee plate, is inserted into a hole which is designed for inserting therein said pin for joining said knee plate and said brake block together.

6. An artificial limb according to claim 1, wherein at least one of said spacer members having said abutment surface being made of resin of a low friction selected from oil-contained resins or phenol resins.

7. An artificial limb according to claim 6, wherein another spacer member adjacent to said spacer member made of resin of a low friction is made of resin selected from polyacetal, polyamide and tetraethylene fluoride.

8. An artificial limb according to claim 1, wherein one of said spacer members supports a resilient member on a surface thereof opposite said abutment surface, and chattering between said spacer means and said load brake means and between said spacer means and said hollow frame is absorbed by resilient deforming force of said resilient member.

9. An artificial limb according to claim 1, wherein said knee axis or said first and second support members is provided with a non-circular recess and the remainder is provided with a protrusion corresponding to said recess, said knee axis being secured to said support members by press fitting said protrusion into said recess.

10. An artificial limb according to claim 1, wherein a cylinder assembly for assisting the walking of the user is disposed between said upper member and said lower member, and said cylinder assembly is located at a rear part of the knee portion, said cylinder assembly being in a reducing stroke where a length of said cylinder is reduced when the knee is bent, said cylinder assembly being in a extending stroke where the length of said cylinder is enlarged when the knee is extended.

11. An artificial limb including a knee joint comprising an upper member including a knee plate to which load of a user of said artificial limb is applied, a lower member including a hollow frame extending from a knee portion towards a foot portion and connected to said upper member at the knee portion, a knee axis for rotatably interconnecting said upper and lower members, opposite end portions of said knee axis being secured to said hollow frame through a first and a second support member, said hollow frame being provided on opposing sides thereof with non-circular first and second attaching holes, said first and second support members being provided respectively with protrusions each having a configuration corresponding to said attaching holes, said first and second support members being secured to said hollow frame by press fitting said protrusions into said attaching holes, respectively, in order to support said knee axis, said artificial limb further comprising:

A. said first and second support members being provided, in addition to said protrusions, with flange portions each having a larger diameter than said protrusions, an end face of each of said protrusions being projected outwardly of an outer surface of said hollow frame when secured to said hollow frame, said flange portion pressing a peripheral edge portion of each of said attaching holes in an inner surface of said hollow frame;

B. said first and second support members, respectively being provided on one surface thereof with grooves which are radially opened, each end portion of said knee axis being attachable to a central portion of each of said support members through said grooves; and C. bolt members coaxial with said knee axis being threadingly joined to end portions of said knee axis, respectively, said bolt members being each provided with a head portion of an enlarged diameter reaching the peripheral edge portion of each of said attaching holes, said hollow frame being supported in a sandwiched fashion between said flange portions of said support members and the head portions of said bolt members.

12. An artificial limb according to claim 11, wherein one surface of the head portion of each of said bolt members opposite said support members is provided with a recess capable of receiving therein said protrusions of said support members which are projected outwardly of the outer surface of said hollow frame, and a ring-shaped protrusion surrounding said recess, said non-circular protrusion of each of said support members being provided with a releasing groove for releasing the protrusion of the head portion of each of said bolt members.

13. An artificial limb according to claim 11 or 12, wherein said hollow frame is made of fiber-reinforced plastic, and said first and second support members including said flange portions and said first and second bolt members including the head portions are made of metal material.

* * * * *